(12) United States Patent
Tanaka et al.

(10) Patent No.: US 6,498,258 B2
(45) Date of Patent: Dec. 24, 2002

(54) 3-ACETYL-N-SUBSTITUTED-3-AMINOMETHYLTETRAHYDROFURAN-2-ONE DERIVATIVE AND PRODUCTION PROCESS THEREFOR

(75) Inventors: Hiroki Tanaka, Arai (JP); Li Rui Pan, Arai (JP); Kiyoshi Ikura, Arai (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/115,949

(22) Filed: Apr. 5, 2002

(65) Prior Publication Data

US 2002/0151727 A1 Oct. 17, 2002

(30) Foreign Application Priority Data

Apr. 10, 2001 (JP) ........................................ 2001-110778

(51) Int. Cl.⁷ ............................................. C07D 307/56
(52) U.S. Cl. ....................................................... 549/321
(58) Field of Search .................................. 549/321, 323

(56) References Cited

FOREIGN PATENT DOCUMENTS

JP        7-60131 A      3/1995

*Primary Examiner*—Amelia Owens
(74) *Attorney, Agent, or Firm*—Birch, Stewart, Kolasch & Birch, LLP

(57) ABSTRACT

A novel 3-acetyl-N-substituted-3-aminomethyltetrahydrofuran-2-one derivative is represented by following Formula (1):

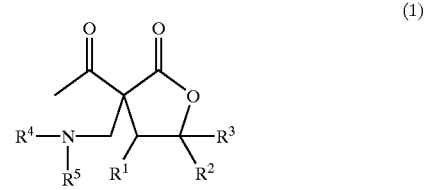

wherein $R^1$, $R^2$ and $R^3$ are the same or different and are each a hydrogen atom or an aliphatic hydrocarbon group; and $R^4$ and $R^5$ are the same or different and are each a hydrogen atom or an arylmethyl group which may have a substituent, where at least one of $R^4$ and $R^5$ is an arylmethyl group which may have a substituent. This compound can be prepared by aminomethylating an 3-acetyltetrahydrofuran-2-one derivative represented by following Formula (2):

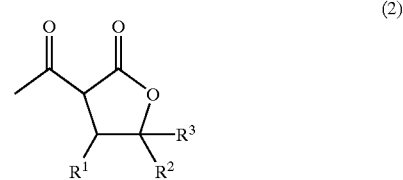

wherein $R^1$, $R^2$ and $R^3$ have the same meanings as above, by a reaction with formaldehyde or a polymer thereof and a primary or secondary amine represented by following Formula (3):

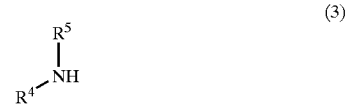

wherein $R^4$ and $R^5$ have the same meanings as above.

6 Claims, No Drawings

3-ACETYL-N-SUBSTITUTED-3-AMINOMETHYLTETRAHYDROFURAN-2-ONE DERIVATIVE AND PRODUCTION PROCESS THEREFOR

BACKGROUND OF THE INVENTION

1. Field of the Invention

The present invention relates to an 3-acetyl-N-substituted-3-aminomethyltetrahydrofuran-2-one derivative and a production process therefor, as well as to production processes for a N-substituted-3-aminomethyltetrahydrofuran-2-one derivative, for an 3-acetyl-3-aminomethyltetrahydrofuran-2-one derivative and for an 3-aminomethyltetrahydrofuran-2-one derivative using the 3-acetyl-N-substituted-3-aminomethyltetrahydrofuran-2-one derivative as a starting material.

2. Description of the Related Art

To produce an analogous compound to 3-aminomethyltetrahydrofuran-2-one, Japanese Unexamined Patent Application Publication No. 7-60131 discloses a process in which 3-methylenetetrahydro-2-(3H)-furanone is allowed to react with diethylamine in the presence of an inorganic compound and thereby yields a N,N-diethyl-aminomethyltetrahydrofuran-2-one. However, the prepared N,N-diethyl-aminomethyltetrahydrofuran-2-one cannot yield 3-aminomethyltetrahydrofuran-2-one by a simple reaction, which 3-aminomethyltetrahydrofuran-2-one is practically used as a pharmaceutical intermediate.

SUMMARY OF THE INVENTION

Accordingly, an object of the present invention is to provide a novel 3-acetyl-N-substituted-3-aminomethyltetrahydrofuran-2-one derivative that is useful for the preparation of an 3-aminomethyltetrahydrofuran-2-one derivative, as well as to provide a production process for the 3-acetyl-N-substituted-3-aminomethyltetrahydrofuran-2-one derivative.

Another object of the present invention is to provide production processes for a N-substituted-3-aminomethyltetrahydrofuran-2-one derivative and for an 3-acetyl-3-aminomethyltetrahydrofuran-2-one derivative, which are useful for the preparation of such an 3-aminomethyltetrahydrofuran-2-one derivative.

A further object of the present invention is to provide a process for efficiently producing an 3-aminomethyltetrahydrofuran-2-one derivative by a simple reaction.

After intensive investigations to achieve the above objects, the present inventors have found that such an 3-aminomethyltetrahydrofuran-2-one derivative can easily be obtained from a novel 3-acetyl-N-substituted-3-aminomethyltetrahydrofuran-2-one derivative. The present invention has been accomplished based on these findings.

Specifically, the present invention provides, in an aspect, an 3-acetyl-N-substituted-3-aminomethyltetrahydrofuran-2-one derivative represented by following Formula (1):

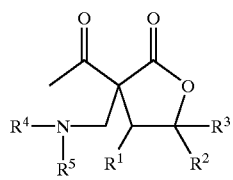

(1)

wherein $R^1$, $R^2$ and $R^3$ are the same or different and are each a hydrogen atom or an aliphatic hydrocarbon group; and $R^4$ and $R^5$ are the same or different and are each a hydrogen atom or an arylmethyl group which may have a substituent, where at least one of $R^4$ and $R^5$ is an arylmethyl group which may have a substituent.

In another aspect, the present invention provides a process for producing the 3-acetyl-N-substituted-3-aminomethyltetrahydrofuran-2-one derivative represented by Formula (1). The process includes the step of subjecting an 3-acetyltetrahydrofuran-2-one derivative represented by following Formula (2):

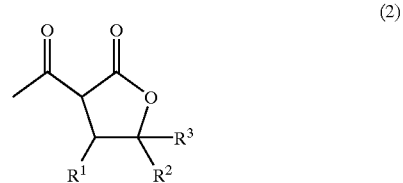

(2)

wherein $R^1$, $R^2$ and $R^3$ are the same or different and are each a hydrogen atom or an aliphatic hydrocarbon group, to aminomethylation by a reaction with formaldehyde or a polymer thereof and a primary or secondary amine represented by following Formula (3):

(3)

wherein $R^4$ and $R^5$ are the same or different and are each a hydrogen atom or an arylmethyl group which may have a substituent, where at least one of $R^4$ and $R^5$ is an arylmethyl group which may have a substituent.

The present invention provides, in a further aspect, a process for producing a N-substituted-3-aminomethyltetrahydrofuran-2-one derivative. The process includes the step of deacetylating the 3-acetyl-N-substituted-3-aminomethyltetrahydrofuran-2-one derivative represented by Formula (1) by a reaction with a base to thereby yield a N-substituted-3-aminomethyltetra- hydrofuran-2-one derivative represented by following Formula (4):

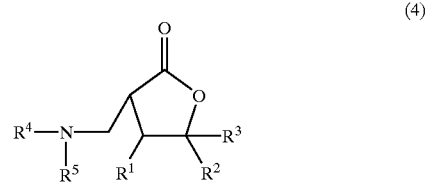

(4)

wherein $R^1$, $R^2$, $R^3$ $R^4$ and $R^5$ have the same meanings as defined above.

In yet another aspect, the present invention provides a process for producing an 3-aminomethyltetrahydrofuran-2-one derivative. The process includes the steps of deacetylating the 3-acetyl-N-substituted-3-aminomethyltetrahydrofuran-2-one derivative represented by Formula (1) by a reaction with a base to thereby yield a N-substituted-3-aminomethyltetrahydrofuran-2-one derivative represented by Formula (4), and subjecting this compound to hydrogenolysis to thereby yield an 3-aminomethyltetrahydrofuran-2-one derivative represented by following Formula (5):

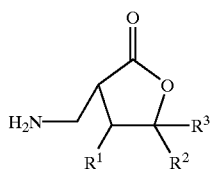

(5)

wherein $R^1$, $R^2$ and $R^3$ have the same meanings as defined above.

In another aspect, the present invention provides a process for producing an 3-acetyl-3-aminomethyltetrahydrofuran-2-one derivative. The process includes the step of subjecting the 3-acetyl-N-substituted-3-aminomethyltetrahydrofuran-2-one derivative represented by Formula (1) to hydrogenolysis to thereby yield an 3-acetyl-3-aminomethyltetrahydrofuran-2-one derivative represented by following Formula (6):

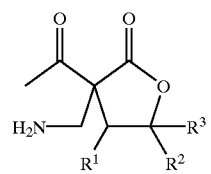

(6)

wherein $R^1$, $R^2$ and $R^3$ have the same meanings as defined above.

Yet another aspect, the present invention provides a process for producing the 3-aminomethyltetrahydrofuran-2-one derivative represented by Formula (5). The process includes the steps of subjecting the 3-acetyl-N-substituted-3-aminomethyltetrahydrofuran-2-one derivative represented by Formula (1) to hydrogenolysis to thereby yield the 3-acetyl-3-aminomethyltetrahydrofuran-2-one derivative represented by Formula (6), and deacetylating the resulting compound by a reaction with a base.

The present invention can easily yield novel 3-acetyl-N-substituted-3-aminomethyltetrahydrofuran-2-one derivatives.

The present invention can easily yield N-substituted-3-aminomethyltetrahydrofuran-2-one derivatives and 3-acetyl-3-aminomethyltetrahydrofuran-2-one derivatives, which are useful for the preparation of the 3-aminomethyltetrahydrofuran-2-one derivatives.

In addition and advantageously, the present invention can efficiently yield 3-aminomethyltetrahydrofuran-2-one derivatives by a simple reaction.

DESCRIPTION OF THE PREFERRED EMBODIMENTS

3-Acetyl-N-substituted-3-aminomethyltetrahydrofuran-2-one Derivatives and Production Thereof In the 3-acetyl-N-substituted-3-aminomethyltetrahydrofuran-2-one derivatives represented by Formula (1), the substituents $R^1$, $R^2$ and $R^3$ are the same or different and are each a hydrogen atom or an aliphatic hydrocarbon group.

Such aliphatic hydrocarbon groups include, but are not limited to, methyl, ethyl, propyl, isopropyl, butyl, isobutyl, s-butyl, t-butyl, pentyl, hexyl, decyl, dodecyl, andotheralkyl groups each having from about 1 to about 10, and preferably from about 1 to about 4, carbon atoms; vinyl, allyl, 1-butenyl, and other alkenyl groups each having from about 2 to about 10, and preferably from about 2 to about 4, carbon atoms; ethynyl, propynyl, and other alkynyl groups each having from about 2 to about 10, and preferably from about 2 to about 4, carbon atoms.

In Formula (1), the substituents $R^4$ and $R^5$ are the same or different and are each a hydrogen atom or an arylmethyl group which may have a substituent, where at least one of $R^4$ and $R^5$ is an arylmethyl group which may have a substituent. The substituent may be substituted on a carbon atom of whichever of the aryl moiety and the methyl moiety of the arylmethyl group. Such aryl groups include aromatic carbocyclic groups and aromatic heterocyclic groups.

Such aromatic carbocyclic groups include, but are not limited to, phenyl, naphthyl, and other aromatic carbocyclic groups each having from about 6 to about 20, and preferably from about 6 to about 10, carbon atoms. The aromatic heterocyclic groups include, for example, pyridyl group.

Substituents which may be substituted on the aryl moiety of the arylmethyl group include, but are not limited to, halogen atoms (e.g., fluorine, chlorine and bromine atoms), oxo group, hydroxyl group, substituted oxy groups (e.g., methoxy group and other alkoxy groups; aryloxy groups; aralkyloxy groups; and acyloxy groups), carboxyl group, substituted oxycarbonyl groups, substituted or unsubstituted carbamoyl groups, cyano group, nitro group, substituted or unsubstituted amino groups, and alkyl groups (e.g., methyl, ethyl, propyl, isopropyl, and other $C_1$–$C_4$ alkyl groups)

Substituents which may be substituted on a carbon atom of the methyl moiety of the arylmethyl group include, but are not limited to, methyl, ethyl, propyl, isopropyl, butyl, and other alkyl groups (preferably, alkyl groups each having from 1 to 4 carbon atoms), the aforementioned aryl groups such as phenyl, naphthyl, pyridyl, and other aromatic carbocyclic groups or aromatic heterocyclic groups which may have a substituent.

In the arylmethyl group, a substituent on the methyl moiety may be combined with the aryl moiety or with a substituent on the aryl moiety to form a ring.

Examples of the arylmethyl group are benzyl, p-chlorobenzyl, p-bromobenzyl, o-nitrobenzyl, p-nitrobenzyl, p-cyanobenzyl, 3,4-dimethoxybenzyl, α-phenylethyl, diphenylmethyl, bis (p-methoxyphenyl) methyl, triphenylmethyl, (p-methoxyphenyl) diphenylmethyl, diphenyl-4-pyridylmethyl, 2-pyridyl-N-oxide, and 5-dibenzosuberyl groups.

The 3-acetyl-N-substituted-3-aminomethyltetrahydrofuran-2-one derivativerepresentedbyFormula (1) can be obtained by allowing an 3-acetyltetrahydrofuran-2-one derivative represented by Formula (2) to react with formaldehyde or a polymer thereof and a primary or secondary amine represented by Formula (3) and thereby introducing a N-substituted aminomethyl group into the 3-position of the 3-acetyltetrahydrofuran-2-one derivative represented by Formula (2).

The substituents $R^1$, $R^2$, $R^3$, $R^4$ and $R^5$ in Formula (2) and (3) include the same groups as mentioned above.

As formaldehyde, pure formaldehyde may be used, but an aqueous solution of formaldehyde (formalin) having a concentration of from about 30% to 50% by weight, and preferably from about 35% to 45% by weight, is advantageously used. The formaldehyde may be formed in a reaction system. Polymers of formaldehyde include, for example, paraformaldehyde and other low molecular weight polyoxymethylenes. The amount of the formaldehyde or a polymer thereof is, as formaldehyde, from about 1 to about 3 moles and preferably from about 1.1 to about 2 moles relative to 1 mole of the substrate 3-acetyltetrahydrofuran-2-one derivative.

A reaction is performed in the presence of, or in the absence of, a solvent. The solvent is not specifically limited, as long as it does not adversely affect the reaction. Such solvents include, but are not limited to, methanol, ethanol, propanol, t-butyl alcohol, and other alcohols; chloroform, dichloromethane, 1,2-dichloroethane, and other halogenated hydrocarbons; benzene and other aromatic hydrocarbons; hexane, heptane, octane, and other aliphatic hydrocarbons; cyclohexane and other alicyclic hydrocarbons; N,N-dimethylformamide, N,N-dimethylacetamide, and other amides; acetonitrile, propionitrile, benzonitrile, and other nitriles; diethyl ether, t-butylmethyl ether, tetrahydrofuran, and other chain or cyclic ethers; ethyl acetate and other esters; acetic acid and other organic acids; and water. Preferred solvents are water; and methanol, ethanol, propanol, and other alcohols, of which water is typically preferred. Each of these solvents can be used alone or in combination.

A reaction temperature can appropriately be set depending on the type of the substrate and other factors and is, for example, from about 10° C. to about 100° C., and preferably from about 20° C. to about 50° C. The reaction smoothly proceeds at around room temperature.

The reaction may be performed at ambient or atmospheric pressure or under a pressure (under a load) in a conventional system such as batch system, semi-batch system or continuous system.

After the completion of the reaction, reaction products can be separated and purified by, for example, filtration, concentration, distillation, extraction, crystallization, recrystallization, adsorption, column chromatography, and other separation means or combinations of these separation means.

Production of N-Substituted-3-aminomethyltetrahydrofuran-2-one Derivatives

The N-substituted-3-aminomethyltetrahydrofuran-2-one derivative represented by Formula (4) can be prepared by deacetylating the 3-acetyl-3-aminomethyltetrahydrofuran-2-one derivative represented by Formula (1) by a reaction with a base.

Such bases for use in the reaction include, but are not limited to, sodium carbonate, potassium carbonate, and other alkali metal carbonates; sodium hydrogencarbonate, potassium hydrogencarbonate, and other alkali metal hydrogencarbonates; sodium hydroxide, potassium hydroxide, and other alkali metal hydroxides; magnesium carbonate, calcium carbonate, and other alkaline earth metal carbonates; magnesium hydrogencarbonate, calcium hydrogencarbonate, and other alkaline earth metal hydrogencarbonates; magnesium hydroxide, calcium hydroxide, and other alkaline earth metal hydroxides; and other inorganic bases. Each of these bases can be used alone or in combination. The amount of the base is from about 0.5 to about 4 moles, and preferably from about 1 to about 2 moles, relative to 1 mole of the substrate 3-acetyl-N-substituted-3-aminomethyltetrahydrofuran-2-one derivative.

The reaction is generally performed in the presence of a solvent. Such solvents are not specifically limited as long as they do not adversely affect the reaction and include the solvents exemplified in the production of the 3-acetyl-N-substituted-3-aminomethyltetrahydrofuran-2-one derivative. Preferred solvents in this reaction are water; methanol, ethanol, propanol, isopropanol, butanol, and other alcohols; diethyl ether, t-butylmethyl ether, and other ethers. The amount of the solvent is, for example, from about 2 to about 30 parts by weight, and preferably from about 3 to about 20 parts by weight, relative to 1 part by weight of the 3-acetyl-N-substituted-3-aminomethyltetrahydrofuran-2-one derivative.

To perform the reaction in a shorter time, a phase transfer catalyst may be added to the reaction system. Such phase transfer catalysts include, but are not limited to, tetraethylammonium chloride, tetraethylammonium bromide, tetrabutylammonium chloride, tetrabutylammonium bromide, tetrabutylammonium iodide, tetraethylammonium hydrogensulfate, tetrabutylammonium hydroxide, tetraoctylammonium chloride, trimethylbenzylammonium chloride, triethylbenzylammonium chloride, tributylbenzylammonium chloride, tributylbenzylammonium bromide, trioctylbenzylammonium chloride, cetyldimethylbenzylammonium chloride, tetrabutylphosphonium chloride, tetrabutylphosphonium bromide, and other conventional phase transfer catalysts. Among them, cetyldimethylbenzylammonium chloride and triethylbenzylammonium chloride are preferred. The amount of the phase transfer catalyst is, for example, from about 0.01 to about 0.3 mole, and preferably from about 0.05 to about 0.1 mole, relative to 1 mole of the substrate 3-acetyl-N-substituted-3-aminomethyltetrahydrofuran-2-one derivative.

A reaction temperature can appropriately be set depending on the type of the substrate and other factors and is, for example, from about 0° C. to about 50° C., and preferably from about 0° C. to about 10° C. The reaction can be performed in a conventional system such as batch system, semi-batch system or continuous system.

After the completion of the reaction, reaction products can be separated and purified by, for example, filtration, concentration, distillation, extraction, crystallization, recrystallization, adsorption, column chromatography, and other separation means or combinations of these separation means.

Production of 3-Acetyl-3-aminomethyltetrahydrofuran-2-one Derivatives

The 3-acetyl-3-aminomethyltetrahydrofuran-2-one derivative represented by Formula (6) can be obtained by subjecting the 3-acetyl-N-substituted-3-aminomethyltetrahydrofuran-2-one derivative represented by Formula (1) to hydrogenolysis (hydrocracking).

The hydrogenolysis is generally performed by bringing the 3-acetyl-N-substituted-3-aminomethyltetrahydrofuran-2-one derivative into contact with hydrogen in a solvent in the presence of a hydrogenolysis catalyst. Such hydrogenolysis catalysts include any conventional hydrogenolysis catalysts, of which a palladium-carbon (activated carbon) catalyst is preferred.

In the palladium-carbon (activated carbon) catalyst, the activated carbon is not specifically limited and includes any activated carbon derived from vegetable materials, mineral materials, polymer materials and other materials by conventional techniques such as gas activation and chemical activation. The activated carbon has a specific surface area of, for example, from about 500 to about 4000 $m^2/g$ and preferably from about 700 to about 4000 $m^2/g$. The amount of palladium on the activated carbon is, for example, from about 1% to about 30% by weight, and preferably from about 3% to about 20% by weight, relative to the weight of the activated carbon.

The amount of the palladium-carbon catalyst is, for example, from about 0.1% to about 20% by weight, and preferably from about 1% to about 10% by weight, relative to the weight of the substrate 3-acetyl-N-substituted-3-aminomethyltetrahydrofuran-2-one derivative.

Hydrogen for use in the hydrogenolysis is not specifically limited and includes pure hydrogen and hydrogen diluted with an inert gas such as nitrogen, argon or helium gas. A gas phase component can be dissolved in a liquid phase by any technique, as long as the gas phase component is sufficiently dissolved in the liquid phase. For example, the gas phase component may be dissolved by gas-liquid contact alone or by blowing a gas containing hydrogen into the liquid phase. Instead of hydrogen, $HCOONH_4$, $HCOONH (C_2H_5)_3$, $NaH_2PO_2$, $NH_2NH_2$ and other hydrogen sources can be used.

The amount of hydrogen can appropriately be set depending on the type of the substrate and other factors and is generally molar excess to the substrate.

Solvents for use in this reaction are not specifically limited as long as they do not adversely affect the reaction and can solve reaction components. Such solvents include, for example, methanol, ethanol, propanol, isopropanol, and other alcohols. The amount of the solvent is generally from about 3 times to about 50 times, and preferably from about 5 times to about 10 times relative to the amount of the substrate.

A reaction temperature is not specifically limited and is preferably from about 10° C. to about 30° C.

The reaction may be performed at atmospheric pressure or under a pressure (under a load). When the reaction is performed under a pressure, the pressure is generally from about 0.1 to about 10 MPa, and preferably from about 0.1 to about 1 MPa. The reaction can be performed in a conventional system such as batch system, semi-batch system or continuous system.

After the completion of the reaction, reaction products can be separated and purified by, for example, filtration, concentration, distillation, extraction, crystallization, recrystallization, adsorption, column chromatography, and other separation means or combinations of these separation means.

Production of 3-Aminomethyltetrahydrofuran-2-one Derivatives

Using the 3-acetyl-N-substituted-3-aminomethyltetrahydrofuran-2-one derivative represented by Formula (1) as a starting material, the 3-aminomethyltetrahydrofuran-2-one derivative represented by Formula (5) can be prepared by either (i) a process via the production of the N-substituted-3-aminomethyltetrahydrofuran-2-one derivative represented by Formula (4) or (ii) a process via the production of the 3-acetyl-3-aminomethyltetrahydrofuran-2-one derivative represented by Formula (6).

The process (i) via the production of the N-substituted-3-aminomethyltetrahydrofuran-2-one derivative represented by Formula (4) includes the steps of (A) yielding the N-substituted-3-aminomethyltetrahydrofuran-2-one derivative represented by Formula (4) from the 3-acetyl-N-substituted-3-aminomethyltetrahydrofuran-2-one derivative represented by Formula (1), and (B) subjecting the resulting compound to hydrogenolysis.

The production process for the N-substituted-3-aminomethyltetrahydrofuran-2-one derivative can be applied as the step (A) of the process (i). In the step (B) of the process (i), the N-substituted-3-aminomethyltetrahydrofuran-2-one derivative as a substrate is subjected to hydrogenolysis in a similar manner as in the production process for the 3-acetyl-3-aminomethyltetrahydrofuran-2-one derivative.

The process (ii) via the production of the 3-acetyl-3-aminomethyltetrahydrofuran-2-one derivative represented by Formula (6) includes the steps of (A) yielding the 3-acetyl-3-aminomethyltetrahydrofuran-2-one derivative represented by Formula (6) from the 3-acetyl-N-substituted-3-aminomethyltetrahydrofuran-2-one derivative represented by Formula (1), and (B) deacetylating the resulting compound by a reaction with a base.

As the step (A) of the process (ii), the production process for the 3-acetyl-3-aminomethyltetrahydrofuran-2-one derivative can be applied. In the step (B) of the process (ii), the 3-acetyl-3-aminomethyltetrahydrofuran-2-one derivative as a substrate is deacetylated by a reaction with a base in a similar manner as in the production process for the N-substituted-3-aminomethyltetrahydrofuran-2-one derivative represented by Formula (4).

EXAMPLES

The present invention will be illustrated in further detail with reference to several examples below, which are not intended to limit the scope of the invention.

In the examples, NMR spectra were determined with tetramethylsilane as an internal standard at 270 MHz ($^1$H-NMR) using JNM-EX270 available from JEOL Ltd. Coupling constants (Hz) are indicated by J.

Example 1

Production of 3-Acetyl-N,N-dibenzyl-3-aminomethyltetrahydrofuran-2-one

To a mixture of 10.2 g of dibenzylamine and 29.7 g of water, 8.9 g of 37% by weight formaldehyde aqueous solution was added dropwise at room temperature, followed by dropwise addition of 12.8 g of 3-acetyltetrahydrofuran-2-one at room temperature. After the completion of addition, the mixture was heated to 90° C. and thereby yielded a solution. The solution was cooled to room temperature, was filtrated, the resulting solid matter was heated with diethyl ether and thereby yielded a solution. The solution was gradually cooled to 0° C., the resulting crystal was filtrated and thereby yielded 19.2 g of 3-acetyl-N,N-dibenzyl-3-aminomethyltetrahydrofuran-2-one as a white crystal.

Spectral Data $^1$H-NMR (CDCl$_3$) ppm: 2.07 (s, 3H, C$\underline{H}_3$CO), 2.11–2.22 (m, OC$\underline{H}_2$CH$_2$), 2.80–2.85 (d, 1H, J=13.5, CC$\underline{H}_2$N), 2.98–3.06 (m, 1H, OC$\underline{H}_2$CH$_2$), 3.25–3.30 (d, 2H, J=13.5, NC$\underline{H}_2$Ph), 3.47–3.52 (d, 1H, J=13.5, CC$\underline{H}_2$N), 3.69–3.74 (d, 2H, J=13.5, NC$\underline{H}_2$Ph), 4.00–4.10 (m, 1H, OC$\underline{H}_2$CH$_2$), 4.17–4.25 (m, 1H, OC$\underline{H}_2$C$\underline{H}_2$), 7.22–7.36 (m, 10H, Ph)

Example 2

Production of 3-Acetyl-N-benzyl-3-aminomethyltetrahydrofuran-2-one

To 59.4 g of water, 21.4 g of benzylamine was added, and the resulting mixture was stirred with 17.8 g of 37% by weight formaldehyde aqueous solution at room temperature for 1 hour. To the mixture, 25.6 g of 3-acetyltetrahydrofuran-2-one was added dropwise, followed by stirring at 60° C. for 1 hour. After the completion of reaction, the resulting mixture was cooled to room temperature, followed by removal of water from the resulting oily matter, and thereby yielded 23.6 g of 3-acetyl-N-benzyl-3-aminomethyltetrahydrofuran-2-one as a yellow oily matter.

Spectral Data $^1$H-NMR (CDCl$_3$) ppm: 2.06–2.22 (m, 1H, C$\underline{H}_2$CH$_2$O), 2.27 (s, 3H, C$\underline{H}_3$), 2.73–2.82 (m, 1H, C$\underline{H}_2$CH$_2$O), 3.01 (d, 1H, J=12.2, NHC$\underline{H}_2$C), 3.13 (d, 1H, J=12.2, NHC$\underline{H}_2$C), 3.77 (s, 2H, NHC$\underline{H}_2$Ph), 4.11–4.30 (m, 2H, CH$_2$C$\underline{H}_2$O)

Example 3

Production of N,N-Dibenzyl-3-aminomethyltetrahydrofuran-2-one

To 6.8 g of 3-acetyl-N,N-dibenzyl-3-aminomethyl-tetrahydrofuran-2-one, 33.8 g of diethyl ether and 0.68 g of cetyldimethylbenzylammonium chloride were added, followed by dropwise addition of 8 g of 10% by weight NaOH aqueous solution at 0° C. The resulting diethyl ether layer was separated, was concentrated under reduced pressure, the residue was subjected to column chromatography on a silica gel, was eluted with hexane-ethyl acetate and thereby yielded 3.45 g of N,N-dibenzyl-3-aminomethyltetra-hydrofuran-2-one as a light yellow liquid.

Spectral Data $^1$H-NMR (CDCl$_3$) ppm: 1.90–2.00 (m, 1H, OCH$_2$C$\underline{H}_2$), 2.30–2.37 (m, 1H, OCH$_2$C$\underline{H}_2$), 2.57–2.61 (m, 1H, CC$\underline{H}_2$N), 2.68–2.80 (m, 1H, $\underline{H}$CCH$_2$N), 2.83–2.89 (dd, 1H, J=3.78, 12.2, CC$\underline{H}_2$N), 3.39–3.44 (d, 2H, J=13.5, NC$\underline{H}_2$Ph), 3.75–3.80 (d, 2H, J=13.5, NC$\underline{H}_2$Ph), 4.09–4.16 (m, 2H, OC$\underline{H}_2$CH$_2$), 7.22–7.36 (m, 10H, Ph)

Other embodiments and variations will be obvious to those skilled in the art, and this invention is not to be limited to the specific matters stated above.

What is claimed is:

1. An 3-acetyl-N-substituted-3-aminomethyl-tetrahydrofuran-2-one derivative represented by following Formula (1):

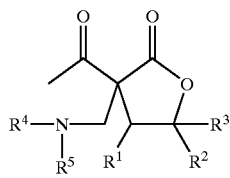

(1)

wherein R$^1$, R$^2$ and R$^3$ are the same or different and are each a hydrogen atom or an aliphatic hydrocarbon group; and R$^4$ and R$^5$ are the same or different and are each a hydrogen atom or an arylmethyl group which may have a substituent, where at least one of R$^4$ and R$^5$ is an arylmethyl group which may have a substituent.

2. A process for producing an 3-acetyl-N-substituted-3-aminomethyltetrahydrofuran-2-one derivative, the process comprising the step of:

subjecting an 3-acetyltetrahydrofuran-2-one derivative resented by following Formula (2):

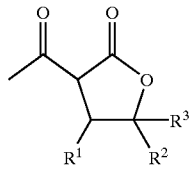

(2)

wherein R$^1$, R$^2$ and R$^3$ are the same or different and are each a hydrogen atom or an aliphatic hydrocarbon group, to aminomethylation by a reaction with formaldehyde or a polymer thereof and a primary or secondary amine represented by following Formula (3):

(3)

wherein R$^4$ and R$^5$ are the same or different and are each a hydrogen atom or an arylmethyl group which may have a substituent, where at least one of R$^4$ and R$^5$ is an arylmethyl group which may have a substituent, to thereby yield an 3-acetyl-N-substituted-3-aminomethyltetrahydrofuran-2-one derivative represented by following Formula (1):

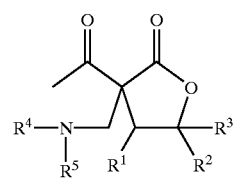

(1)

wherein R$^1$, R$^2$, R$^3$, R$^4$ and R$^5$ have the same meanings as defined above.

3. A process for producing a N-substituted-3-aminomethyltetrahydrofuran-2-one derivative, the process comprising the step of:

deacetylating an 3-acetyl-N-substituted-3-aminomethyl-tetrahydrofuran-2-one derivative represented by following Formula (1):

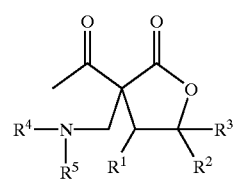

(1)

wherein R$^1$, R$^2$ and R$^3$ are the same or different and are each a hydrogen atom or an aliphatic hydrocarbon group; and R$^4$ and R$^5$ are the same or different and are each a hydrogen atom or an arylmethyl group which may have a substituent, where at least one of R$^4$ and R$^5$ is anarylmethyl group which may have a substituent, by a reaction with a base to thereby yield a N-substituted-3-aminomethyltetrahydrofuran-2-one derivative represented by following Formula (4):

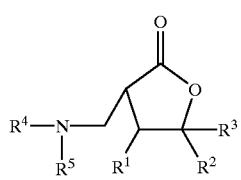

(4)

wherein R$^1$, R$^2$, R$^3$, R$^4$ and R$^5$ have the same meanings as defined above.

4. A process for producing 3-aminomethyltetra-hydrofuran-2-one derivative, the process comprising the steps of:

deacetylating an 3-acetyl-N-substituted-3-aminomethyl-tetrahydrofuran-2-one derivative represented by following Formula (1):

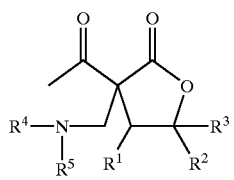

(1)

wherein $R^1$, $R^2$ and $R^3$ are the same or different and are each a hydrogen atom or an aliphatic hydrocarbon group; and $R^4$ and $R^5$ are the same or different and are each a hydrogen atom or an arylmethyl group which may have a substituent, where at least one of $R^4$ and $R^5$ is an arylmethyl group which may have a substituent, by a reaction with a base to thereby yield a N-substituted-3-aminomethyltetrahydrofuran-2-one derivative represented by following Formula (4):

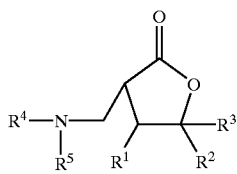

(4)

wherein $R^1$, $R^2$, $R^3$, $R^4$ and $R^5$ have the same meanings as defined above; and subjecting the N-substituted-3-aminomethyl-tetrahydrofuran-2-one derivative represented by Formula (4) to hydrogenolysis to thereby yield an 3-aminomethyltetrahydrofuran-2-one derivative represented by following Formula (5):

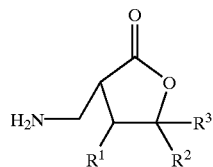

(5)

wherein $R^1$, $R^2$ and $R^3$ have the same meanings as defined above.

5. A process for producing an 3-acetyl-3-aminomethyltetrahydrofuran-2-one derivative, the process comprising the step of:

subjecting an 3-acetyl-N-substituted-3-aminomethyl-tetrahydrofuran-2-one derivative represented by following Formula (1):

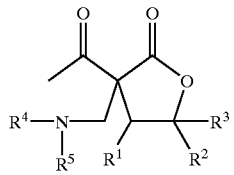

(1)

wherein $R^1$, $R^2$ and $R^3$ are the same or different and are each a hydrogen atom or an aliphatic hydrocarbon group; and $R^4$ and $R^5$ are the same or different and are each a hydrogen atom or an arylmethyl group which may have a substituent, where at least one of $R^4$ and $R^5$ is an arylmethyl group which may have a substituent, to hydrogenolysis to thereby yield an 3-acetyl-3-aminomethyltetrahydrofuran-2-one derivative represented by following Formula (6):

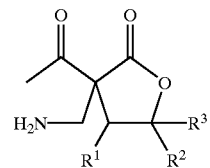

(6)

wherein $R^1$, $R^2$ and $R^3$ have the same meanings as defined above.

6. A process for producing an 3-aminomethyl-tetrahydrofuran-2-one derivative, the process comprising the steps of:

subjecting an 3-acetyl-N-substituted-3-aminomethyl-tetrahydrofuran-2-one derivative represented by following Formula (1):

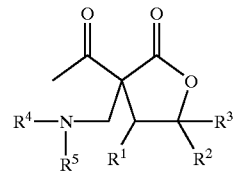

(1)

wherein $R^1$, $R^2$ and $R^3$ are the same or different and are each a hydrogen atom or an aliphatic hydrocarbon group; and $R^4$ and $R^5$ are the same or different and are each a hydrogen atom or an arylmethyl group which may have a substituent, where at least one of $R^4$ and $R^5$ is an arylmethyl group which may have a substituent, to hydrogenolysis to thereby yield an 3-acetyl-3-aminomethyltetrahydrofuran-2-one derivative represented by following Formula (6):

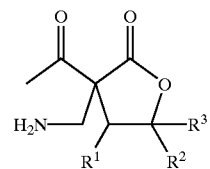

(6)

wherein $R^1$, $R^2$ and $R^3$ have the same meanings as defined above; and deacetylating the 3-acetyl-3-aminomethyltetra-hydrofuran-2-one derivative represented by Formula (6) by a reaction with a base to thereby yield an 3-aminomethyltetrahydrofuran-2-one derivative represented by following Formula (5):

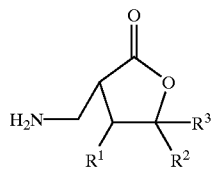

(5)

wherein $R^1$, $R^2$ and $R^3$ have the same meanings as defined above.

* * * * *